(12) United States Patent
White

(10) Patent No.: US 7,823,460 B2
(45) Date of Patent: Nov. 2, 2010

(54) PROSTHETIC SIMULATOR WITH SOFT TISSUE MODELING

(75) Inventor: Bruce F. White, Natick, MA (US)

(73) Assignee: Advanced Mechanical Technology, Inc., Watertown, MA (US)

( * ) Notice: Subject to any disclaimer, the term of this patent is extended or adjusted under 35 U.S.C. 154(b) by 186 days.

(21) Appl. No.: 11/503,867

(22) Filed: Aug. 14, 2006

(65) Prior Publication Data

US 2007/0051180 A1 Mar. 8, 2007

Related U.S. Application Data

(60) Provisional application No. 60/707,773, filed on Aug. 12, 2005.

(51) Int. Cl.
*G01N 19/00* (2006.01)
(52) U.S. Cl. .................................................. 73/804
(58) Field of Classification Search .................. 73/804, 73/806, 7, 760, 781, 778; 600/16, 17; 623/3; 33/534
See application file for complete search history.

(56) References Cited

U.S. PATENT DOCUMENTS

| | | | | |
|---|---|---|---|---|
| 3,536,423 | A * | 10/1970 | Robinson | 417/394 |
| 3,555,252 | A | 1/1971 | Garden | |
| 5,155,423 | A * | 10/1992 | Karlen et al. | 318/568.11 |
| 5,888,242 | A * | 3/1999 | Antaki et al. | 623/3.28 |
| 5,937,530 | A * | 8/1999 | Masson | 33/534 |
| 6,131,436 | A * | 10/2000 | O'Bannon et al. | 73/7 |
| 6,872,187 | B1 * | 3/2005 | Stark et al. | 602/16 |
| 6,979,164 | B2 * | 12/2005 | Kramer | 414/5 |
| 7,090,650 | B2 * | 8/2006 | Ou et al. | 601/5 |
| 7,201,728 | B2 * | 4/2007 | Sterling | 602/16 |
| 7,206,626 | B2 * | 4/2007 | Quaid, III | 600/407 |
| 7,383,738 | B2 * | 6/2008 | Schulz | 73/781 |
| 7,386,366 | B2 * | 6/2008 | Dariush | 700/245 |

(Continued)

OTHER PUBLICATIONS

Zheng, D., et al., "Nonlinear Adaptive Learning for Electrohydraulic Control Systems," Department of Mechanical & Industrial Engineering, University of Illinois, Urbana-Champaign, supported by NSF DMI96-24837CARREER and ONR N00014-96-1-0754.

(Continued)

*Primary Examiner*—Lisa M Caputo
*Assistant Examiner*—Octavia Davis
(74) *Attorney, Agent, or Firm*—Hamilton, Brook, Smith & Reynolds, P.C.

(57) ABSTRACT

A virtual soft tissue control system that provides enhanced motion control to a prosthetic simulator machine. The control system advantageously adds a "virtual soft tissue" control scheme to a conventional control system, such as a digital proportional integral derivative (PID) controller, to algorithmically model the soft tissue constraints that would be encountered by the prosthesis within the human body, and account for these forces in driving the simulator. In another aspect, a prosthetic simulator comprises a prosthetic drive mechanism; a feedback control system that drives the prosthetic drive mechanism; and an iterative learning control system that determines an error from a previous iteration of motion of the drive mechanism and uses the error to determine a drive signal for a subsequent iteration of motion. In certain embodiments, the prosthetic simulator uses both a soft tissue model and an iterative learning control system.

17 Claims, 8 Drawing Sheets

U.S. PATENT DOCUMENTS

2004/0254771 A1* 12/2004 Riener et al. .................. 703/7

OTHER PUBLICATIONS

Walker, P. S., et al., "A Knee Simulating Machine for Performance Evaluation of Total Knee Replacements," *J. Biomechanics*, 30(1): 83-89 (1997).

Cheah, C., et al., "Learning Impedance Control for Robotic Manipulators," *IEEE Transactions on Robotics and Automation*, 14(3): 452-465 (1998).

Stramigioli, S., et al., "A Rigorous Framework for Interactive Robot Control," *Int. J. Control*, 75(18): 1486-1503 (2002).

Chen, Y., et al., "Interactive Learning Control with Iteration-Domain Adaptive Feedforward Compensation," IEEE CDC'03 as a regular paper. (Feb. 2003). *IEEE 2003 Conference on Decision and Control*, Dec. 9-12, 2003 (Hawaii).

Doh, T.-Y., et al., "Repetitive Control Design for Linear Systems with Time-Varying Uncertainties," *IEEE Proc.-Control Theory Appl.*, 150(4): 427-432 (2003).

Ferretti, G., "Impedance Control for Elastic Joints Industrial Manipulators," *IEEE Transactions on Robotics and Automation*, 20(3): 488-497 (2004).

Walker, P. S., et al., "Methodology for Long-Term Wear Testing of Total Knee Replacements," *Clinical Orthapedics and Related Research*, 1(372): 1-10 (2000).

White, B. et al., "Multiaxis Joint Simulator with Software Implemented Soft Tissue Simulation," *Proceedings from the Materials & Processes for Medical Devices Conference*, Sep. 8-10, 2003, Anaheim, CA, ASM International, 2004, pp. 240-243.

* cited by examiner

PROSTHETIC SIMULATOR WITH SOFT TISSUE MODELING

RELATED APPLICATION

This application claims the benefit of U.S. Provisional Application No. 60/707,773, filed on Aug. 12, 2005. The entire teachings of the above application are incorporated herein by reference.

GOVERNMENT SUPPORT

The invention was supported, in whole or in part, by a grant 1 R42 AR051229-01 from the Department of Health and Human Services. The Government has certain rights in the invention.

BACKGROUND OF THE INVENTION

Prosthetic implant failure mechanisms are numerous. Among the most prevalent causes of failure are polyethylene wear, aseptic loosing, infection, and malalignment. Polyethylene wear comprises the largest single identifiable cause of implant failure today. Moreover, polyethylene wear can predispose implants to loosing as a result of increased loading of the reformed tissues. Also, as implant technology evolves, new and more complex modes of wear, damage and failure are being identified. As a consequence of these facts, there is a great need for rigorous implant life cycle testing in simulator machines that are capable of replicating the subtleties of human motion.

Simulator machines address the implant longevity problem by providing a non-human environment in which to evaluate new and existing prosthetic devices through accelerated life testing. These machines allow researchers to isolate and study design deficiencies, identify and correct materials problems, and ultimately to provide the physician and patient with longer life prosthetic systems. Simulator machines approximate human joint motion, and clearly, the closer the approximation the more reliable the results.

To date, simulator machines have at best provided only a very rough approximation of the complexity of human joint motion, such as knee motion. So-called displacement controlled machines rely on an a priori description of the kinematics of the relevant body part, making little or no allowance for variations in prosthetic design, and subject the implant device to these prescribed motions for the duration of the life cycle test. Other machines use a force control system that subjects the prosthetic device to an ensemble of forces and torques which represent those encountered in the body part (e.g. a knee) during physiologic motion. Once implanted in the patient, however, the prosthetic is supported and constrained by the soft tissues of the body. Hence, for improved accuracy, force controlled machines should in some way simulate the natural constraints of these soft tissue forces. Some simulator machines have attempted to provide such constraints with a complex system of mechanical springs. However, these springs have proven cumbersome to work with, and have only a limited capability of simulating the complex characteristics of the human body, such as the knee's soft tissue.

SUMMARY OF THE INVENTION

In one aspect, the present invention is directed to a virtual soft tissue control system that provides enhanced motion control to a prosthetic simulator machine. The prosthetic simulator provides a non-human environment in which to evaluate new and existing prosthetic devices, particularly implantable prosthetic devices, through accelerated life testing. The prosthetic simulator can be used to closely approximate the conditions within the body, particularly with respect to human joints, and can be used to test and evaluate prosthetics for use in various parts of a human body, such as the knees, hips, shoulders, elbows, spines, ankles, hearts or heart valves, or any other articulating components of a human body.

In one embodiment, the invention relates to a prosthetic simulator that comprises a prosthetic drive mechanism; a sensor for measuring the force or torque applied to the prosthetic; and a control system responsive to the sensor and to a simulation input, wherein the control system includes a soft tissue model to account for soft tissue action to drive the drive mechanism. The control system advantageously adds a "virtual soft tissue" control scheme to a conventional control system, such as a digital proportional integral derivative (PID) controller, to algorithmically model the soft tissue constraints that would be encountered by the prosthesis within the human body, and account for these forces in driving the simulator.

In another aspect, the invention relates to a control system for use in a prosthetic simulator, wherein the control system comprises a soft tissue model.

In yet another aspect, the invention relates to a prosthetic simulator that comprises a prosthetic drive mechanism; a feedback control system that drives the prosthetic drive mechanism; and an iterative learning control system that determines an error from a previous iteration of motion of the drive mechanism and uses the error to determine a drive signal for a subsequent iteration of motion. In certain embodiments, the prosthetic simulator uses both a soft tissue model and an iterative learning control system.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of preferred embodiments of the invention follows.

In one aspect, the present invention relates to prosthetic simulators, and in particular, methods and systems for controlling prosthetic simulators. The prosthetic simulator can be used to closely approximate the conditions within the body, particularly with respect to human and animal joints, and can be used to test and evaluate prosthetics for use in various parts of a human or animal body. In the following description, a simulator for testing prosthetic knees is described, though it will be understood that the principles and embodiments described herein are readily applicable to prosthetic simulator devices for the hips, shoulders, elbows, spines, ankles, hearts or heart valves, or any other articulating components of a human or animal body.

Figure 1:
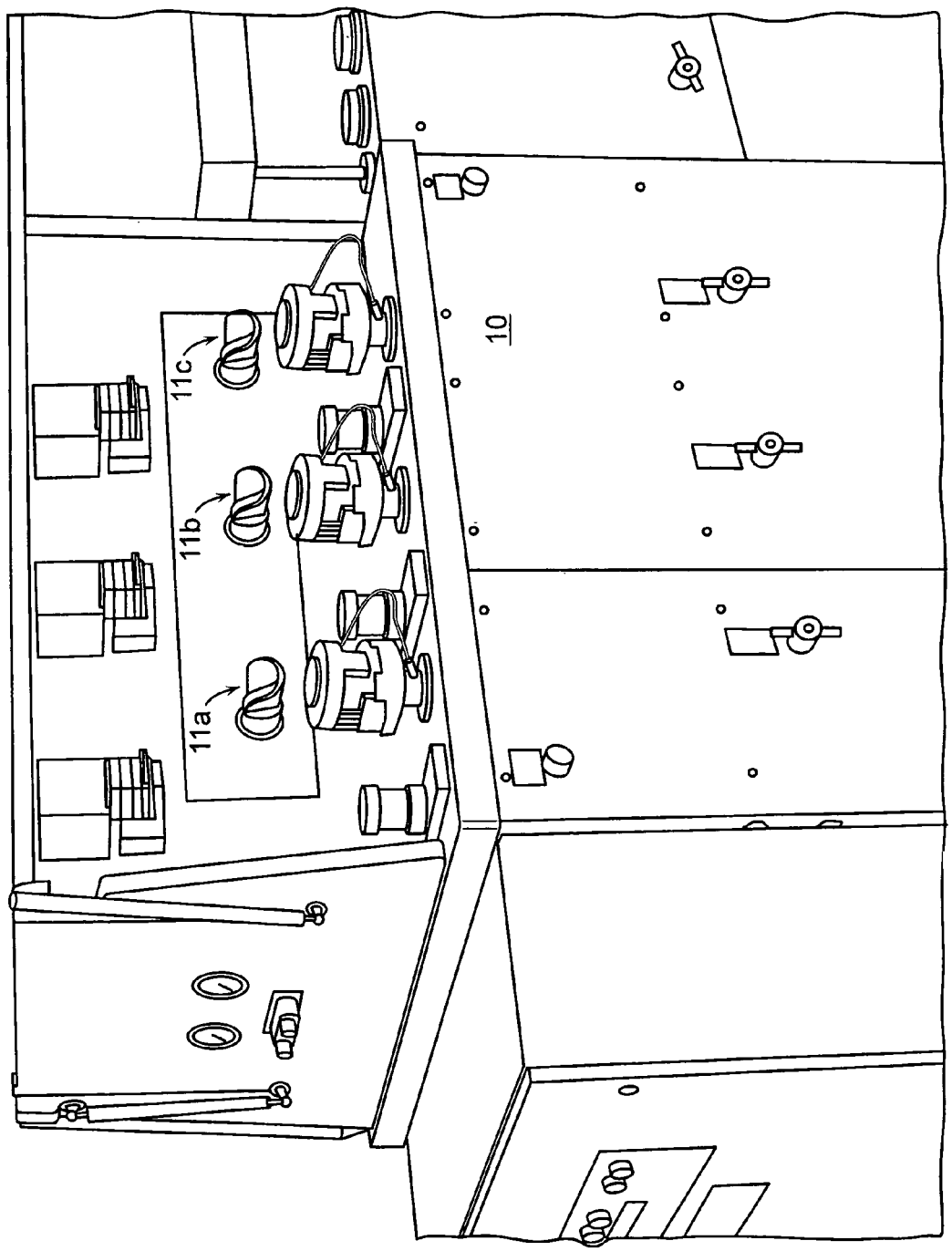
FIG. 1 illustrates a prosthetic simulator machine according to one embodiment of the invention.

An exemplary embodiment of a prosthetic simulator machine 10 is shown in FIG. 1. The prosthetic simulator is used to test prosthetic devices, particularly implant devices, such as prosthetic knees, in a manner that approximates the conditions within the human body. The simulator is preferably capable of performing "accelerated wear" tests, in which the prosthesis is put through a large number of cycles (e.g. 20 million cycles) of pre-determined motions that are likely to be encountered in the human body. In the embodiment shown in FIG. 1, the simulator comprises three stations 11a, 11b, 11c, each having one or more actuators, such as servo-hydraulic actuators, for driving a prosthesis to simulate various types of body motions. It will be understood that a simulator according to the invention can have any number of stations.

Figure 2:
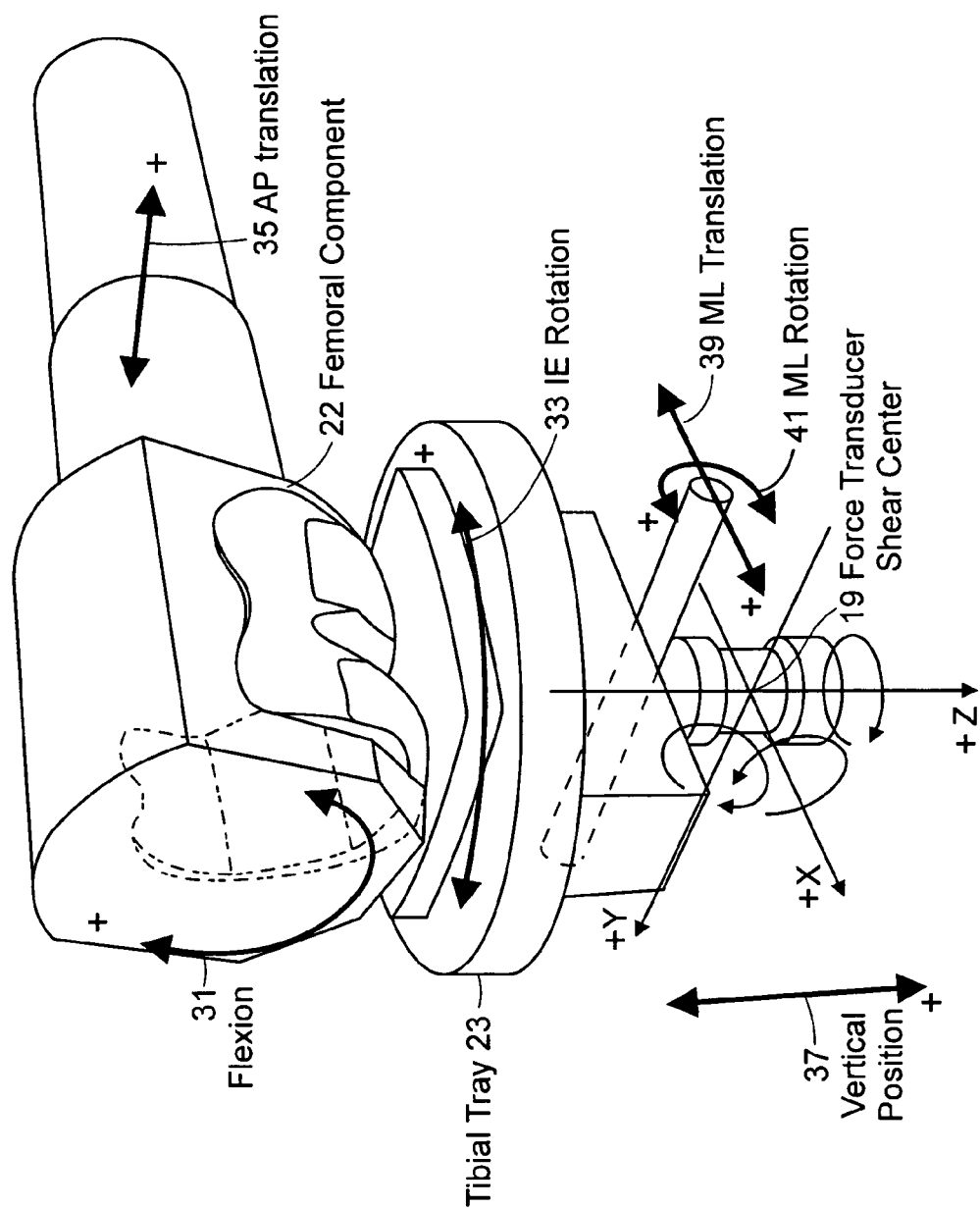
FIG. 2 is a schematic illustration of a simulator stage for a prosthetic device.

An example of a simulator station 11 for a prosthetic knee implant is shown schematically in FIG. 2. This schematic illustrates the typical controlled and uncontrolled degrees of freedom of the knee simulator. Force control of knee simulators relies on the principle of equipollence to reduce the complex system of forces acting across the knee to a system of orthogonal forces consistent with the actions of the machine's mechanical actuators. The forces across the knee may be aggregated into three groups: 1) the active forces of the musculature; 2) the passive forces of the ligamentous and capsular structures; and 3) the contact forces acting on the articular surface.

In prior simulation devices, the machine's actuators have been used to simulate the active forces, a hardware constraint system (such as a mechanical spring arrangement) is used to simulate the passive forces, and the contact forces result directly from tibial-femoral contact.

In one aspect of the present invention, a virtual soft tissue control system utilizes similar partitioning of the forces but adopts a flexible model-based software system rather then the simple mechanical spring arrangement for soft tissue constraint. The modeled soft tissue constraint provides the opportunity for realistic soft tissue approximation incorporating nonlinear, asymmetric features of the soft tissue forces, as discussed below.

Figure 3:
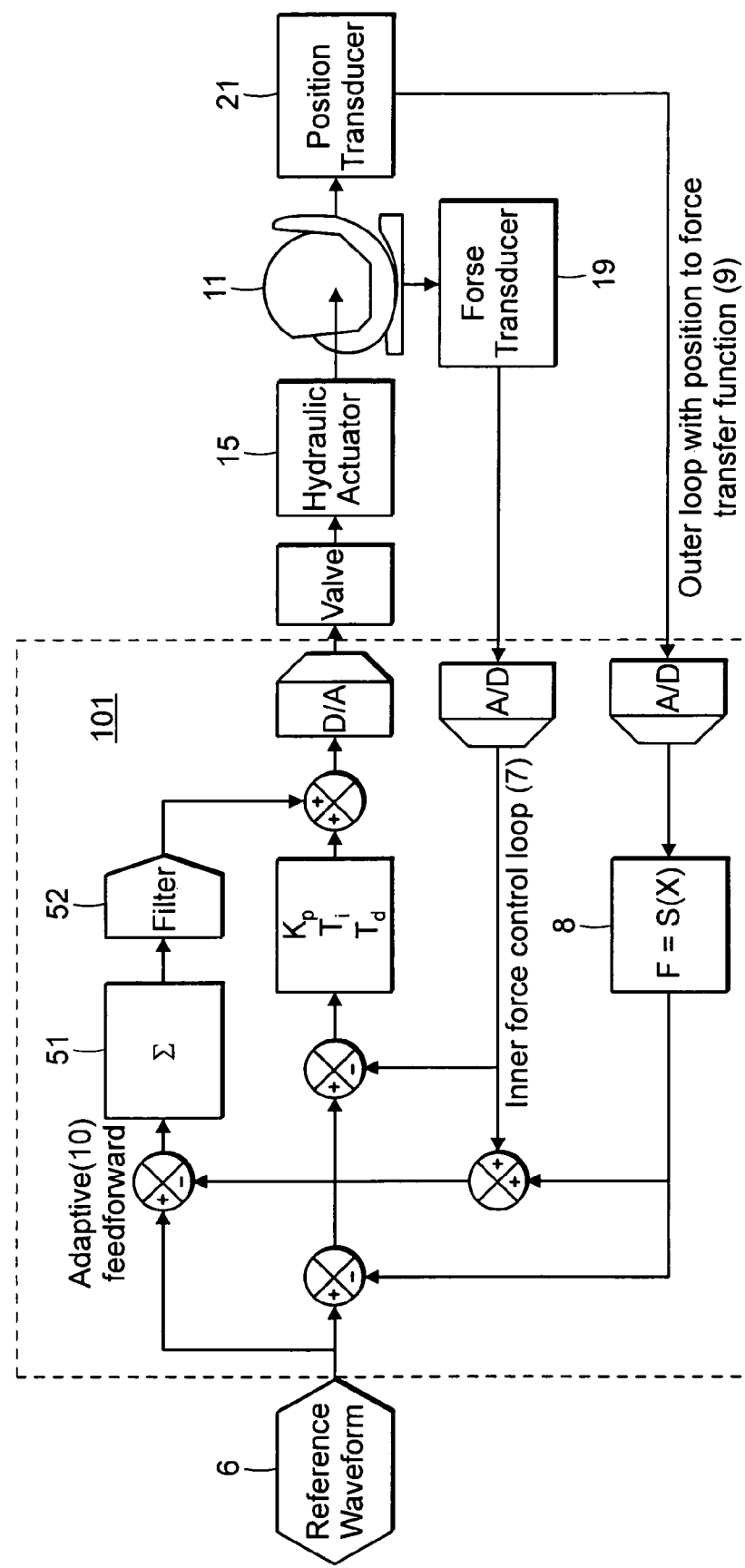
FIG. 3 is a schematic of a control system for a prosthetic simulator in accordance with one embodiment of the invention.

A schematic of a control system for a prosthetic simulator according to one embodiment is shown in FIG. 3. The prosthetic simulator stage 11 is driven by one or more servo-hydraulic actuators 15 under the control of a digital control system 101. As described in further detail below, the control system according to this embodiment includes both a virtual soft tissue model system, and an iterative learning control system.

The simulator includes a multi-axis force/torque transducer 19 mounted beneath the tibial tray of the simulator stage so that the three components of femoral-tibial contact force (and moment) can be monitored. Transducer 19 can be a six-channel strain gauge transducer. In addition, the simulator can include one or more position sensors or transducers 21 to measure the relative translational and rotational positions of the femoral 22 and tibial 23 components of the simulator. As shown in FIG. 2, the position sensor preferably monitors the flexion/extension angle 31, internal/external (IE) rotation angle 33, anterior/posterior (AP) translation 35, and vertical (compression/distraction) position 37 of the prosthesis. The medio-lateral (ML) knee translation 39 and rotation 41 can also be monitored.

As shown in FIG. 3, the force transducer 19 and position sensor(s) 21 provide feedback data regarding the forces and motions of the prosthesis at the simulator stage 11.

The virtual soft tissue control system is comprised of a nested loop design similar to that used in impedance control systems. The inner loop 7 of this nested loop design derives its feedback from the multi-axis force/torque transducer 19. This loop 7 provides traditional proportional, integral, derivative control (PID) via a discrete numeric algorithm. This loop provides force control of the servo-hydraulic actuator 15. An input to this loop represents a force set point or time varying force waveform. Under force control alone the closed loop servo-hydraulic system will attempt to drive the machine's actuator until the output of the force transducer is equal to the force set point.

The virtual soft tissue algorithm is implemented in the outer loop 9 of the nested loop design. This loop derives its feedback from a position transducer 21, or an angular position transducer in the case of interior-exterior (IE) rotation. This position feedback provides the input to a piecewise cubic spline interpolation algorithm 8 that, by proper choice of coefficients, can be programmed to represent the variety of soft tissue force displacement relationships encountered in a human body. The spline coefficients can be calculated offline, based on the desired soft tissue model, and subsequently downloaded to the controller. The cubic spline algorithm is shown schematically by the transfer function: $F=S(x)$ on the diagram in FIG. 3. The spline interpolation algorithm establishes a relationship between the current configuration of the simulator device (where configuration means the relative positions and orientation of the prosthetic components) and the constraint force which emulates the elastic restoring force of the knee's soft tissue. The calculated constraint force is subtracted from the reference force or torque waveform 6, and the residual is passed to the input of the inner loop 7, where it becomes the reference input to the force control portion of the control scheme.

Each controlled degree of freedom is equipped with its own independent control loop, a single channel of which is schematically depicted in FIG. 3. In certain embodiments, a single control variable drives each of the spline approximation algorithms. In other embodiments, multiple inputs can be used to accommodate the complexity of the articulations of the knee.

In one embodiment, the digital signal processor code implements eight synchronized arbitrary waveform generators which are used to provide the driving signals for the simulator's actuators 15. Each waveform generator is programmed via a 256 point array of data downloaded from the PC. This data provides a template for the repetitive control of the associated DAC and the connected actuator. A 24 bit phase generator scheme provides waveform periods from several hours to 0.33 seconds. The waveform generator can utilize a first order interpolation scheme to determine intermediate values between template array points. The waveform generator outputs may be mapped to PID calculation block inputs.

In one embodiment, eight PID calculation blocks which implement the parallel form PID control algorithm are available to provide closed loop control of the machine's actuators. The PID calculation block inputs may be mapped to either a waveform generator block or another PID calculation block. Similarly the PID calculation outputs may be mapped to another PID block input or directly to the systems output DACs. The PID calculation is implemented as shown in equation (a) below:

$$v_o = k_p e(t) = \frac{1}{t_i} \int e(t)dt + td\frac{d}{dt}e(t) \quad (a)$$

where $v_o$ is the output voltage, $k_p$ is the proportional gain constant, $t_i$ is the integral time constant, $t_d$ is the derivative time constant and $e(t)$ is the error signal (the difference between the reference input and the feedback signals).

The soft tissue model is implemented as shown schematically in FIG. 3 by cascading two PID control blocks. The inner loop PID calculation block is setup to provide traditional force control of the servo-hydraulic actuator by selecting the appropriate force or torque channel for feedback. The outer loop feedback source is acted upon by a cubic function as follows:

$$F = a_0 + a_1 x + a_2 x^2 + a_3 x^3 \quad (b)$$

In this way a position input is transformed into a constraining force analogous to the expected constraint of the soft tissue. The soft tissue model is implemented as an eight segment cubic spline algorithm. The input to the algorithm is the user selected displacement input. Typically this will be the AP position signal or the IE angular position signal. The spline calculation is implemented as shown in equation (c). The coefficients $a_{jk}$ and the knots $t_k$ can be determined offline by the virtual soft tissue software on a PC when the programmed soft tissue model is downloaded to the control processor. A lookup table for the coefficients is indexed by the current value of x returned from the selected displacement transducer. Once the coefficients are determined the cubic equation is evaluated via a computationally efficient form which requires only three multiply and accumulate cycles in the DSP. In one embodiment, the following equation specifies the cubic spline algorithm:

$$F = \begin{cases} a_{00} + a_{10}x + a_{20}x^2 + a_{30}x^3 \\ a_{01} a_{11}x + \\ \dots \\ a_{0k} + a_{1k}x + a_{2k}x^2 + a_{3k}x^2 \end{cases} \text{for} \begin{cases} t_o \le x < t_1 \\ t_1 \le x < t_2 \\ \\ t_{k-1} \le x < t_k \end{cases} \quad (c)$$

An additional feature of the present control scheme is the inclusion of an iterative learning control algorithm 10 that wraps around both the inner and outer loops of the control scheme. The iterative learning control algorithm (sometimes called adaptive feed forward) provides extremely accurate tracking performance with little operator adjustment. This aspect of the control system is not necessary to the virtual soft tissue implementation but it greatly enhances the overall usability of the system. Iterative learning control is also applicable to simulator control schemes that do not include a virtual soft tissue feature.

The iterative learning control algorithm 10 is shown schematically in FIG. 3. Iterative learning control relies on the cyclic nature of the control scenario. The error from the previous iteration of motion is used to determine the drive signal for the next iteration. In some ways this concept acts like proportional gain in traditional feedback control but provides a significant advantage. Traditionally, proportional loop gain provides a corrective signal that is proportional to the error signal. Tracking is hampered by the fact there is an inherent lag between the application of the corrective signal and the response of the machine. If the lag is sufficiently large then the phase relationship between the corrective signal and the actuator response can approach 180 degrees. At that point positive reinforcement of the error will occur and instability will ensue. Higher loop gains tend to compound this problem and there results a practical maximum gain which can be applied to the system.

Iterative learning control circumvents this issue by using an error measurement made during a previous iteration of the cycle which is then applied in a precisely synchronized manner in the next iteration of the process. Assuming that the error is both cyclic and deterministic, that it is not due to a random event unsynchronized with the desired repetitive process, then the corrective signal applied at this latter point in time can drive the machine's actuators closer to a perfect error free solution. If the correction technique is applied iteratively it should be possible to eliminate the control error all together. In reality there are many sources of system noise that are not deterministic and are not synchronized with the desired process, and there can be other systematic errors of measurement and calculation that can result in system error. Nonetheless, iterative learning control has been found to be of extraordinary benefit in the control of prosthetic device simulator machines.

In one embodiment, the iterative learning control algorithm is implemented on a PC. Data is gathered representing one repetition of the cyclic motion. The error is calculated as the difference between the driving waveform and the resulting force or motion. The error signal is multiplied by a user set gain value and then accumulated in the adaptive feed-forward accumulator 51. The accumulator is then filtered with a zero phase shift filter 52 (forward backward time sequenced through a Bessle filter) resulting in a smoothed phase coherent drive signal that is then down loaded to the DSP's feed-forward storage table. As the waveform phase generator advances it indexes into the feed-forward table as well. A similar linear interpolation procedure is used to calculate the intermediate feed-forward values which are added to the drive signal in the output stage of the DSP's calculations. Over time this corrective signal reduces the error to nearly negligible levels without significant operator intervention.

Figure 4:
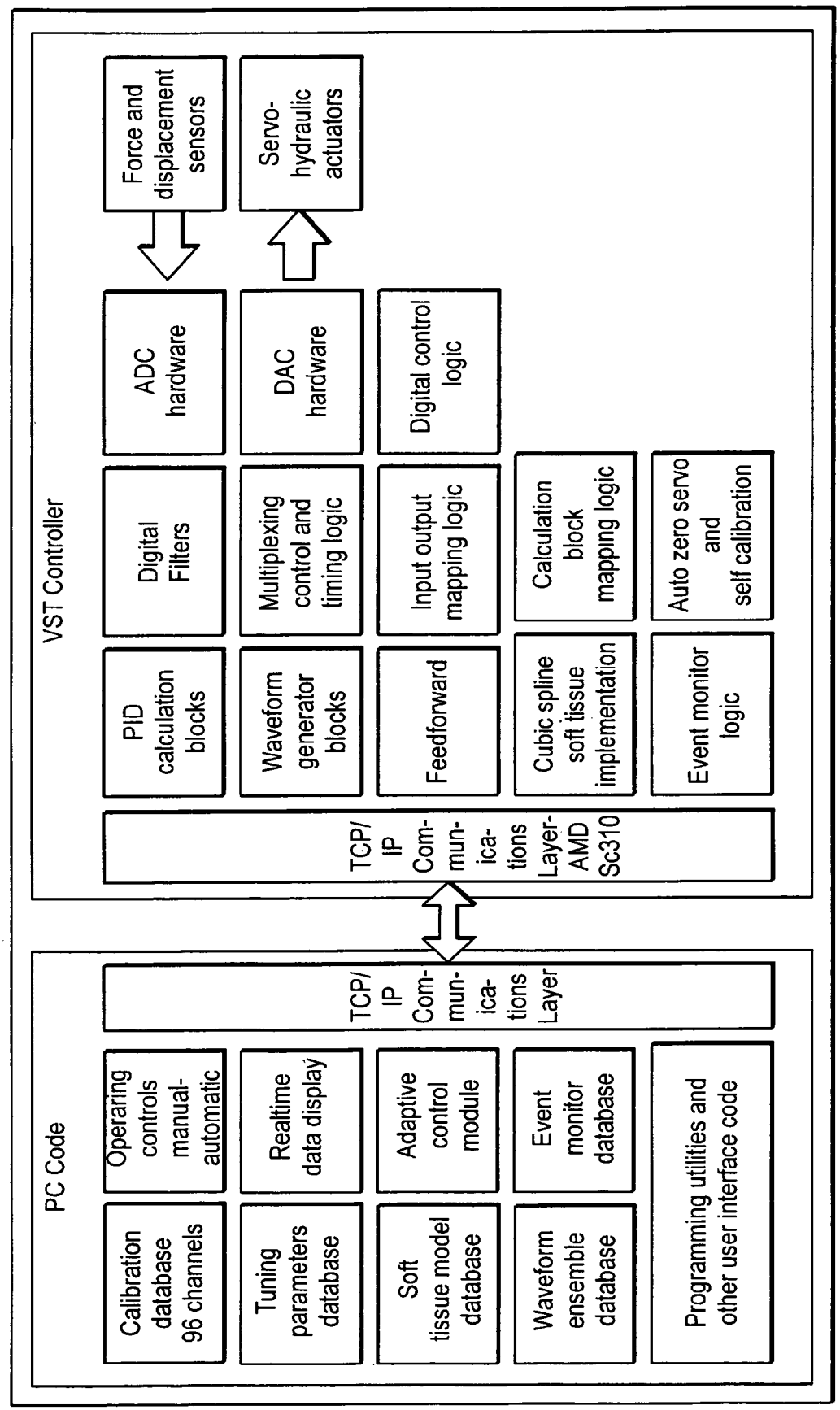
FIG. 4 is a schematic block-diagram showing various subsystems of a control system for a prosthetic device simulator machine.

In certain embodiments, the control system of the present invention can be comprised of several subsystems as illustrated schematically in FIG. 4. Software running on a PC provides the user interface and manages the databases for the calibration information, the waveform ensemble, the control loop tuning information, and the soft tissue model. It also provides the adaptive control algorithm (iterative learning control). Data and control communications between the digital signal processor (DSP) and PC are carried out over an Ethernet physical layer via TCP/IP. The DSP sub-system handles all the real time control and data acquisition tasks. A flexible modular arrangement of calculation and control blocks makes it possible to allocate DSP resources to optimally configure the system for different tasks and different simulator hardware scenarios. The system is designed to interface with single and multi station simulator machines, supporting up to twelve stations of control and data acquisition.

A multi processor architecture can be used to implement the virtual soft tissue control system to provide real time reliability and future extensibility. An AD2181 DSP digital signal processor from Analog Devices, Inc. can provide the core functionality for the real time control and data acquisition system. For coding efficiency, a symmetrical implementation of four channels of control can be implemented where each channel provides a traditional linear PID (proportional, integral, derivative) control algorithm with a sample update rate of 2000 Hz per channel, for example.

The control system can also comprise user interface software that provides, for example, the following functions:

Maintains operating database

Provides TCP/IP communications with VST controller

Provides user interface for editing driving waveforms and soft tissue model

Provides real time data display for setup, tuning and monitoring the machine

Provides program interface to sequence different physiologic motions

Provides event monitoring and event response programming

The operating database can maintain all of the information necessary to control the simulator machine during the course of operation. At the root of this database is the machine calibration file which contains records which include the sensibility, excitation level, amplification level, and labeling for every electromechanical transducer designed into the simulator machines hardware. The calibration database also maintains records for the interpretation of various digitally synthesized signals that are returned from the VST controller including the waveform data and actuator drive signals. When setup to control a single station simulator the calibration database contains 39 records and when setup to control a six station knee machine 96 records are necessary. The calibration database is designed to maintain all of the machine specific or hardware specific information about the simulator system.

Next in line in the organization of the database is the tuning and mapping configuration data that establishes how the control system will run. This part of the database establishes the control relationships for the system such as the feedback mapping an source input mapping for each of the controller's output DACS. The required control paradigm, such as force control, displacement control, open loop control or virtual soft tissue control can be established for each of the controllers output channels. Feedback sources for control may be selected from the various measured system variables. Once the basic system configuration is established then specific tuning parameters such as proportional gain, integral time constant and derivative gain may be set. If virtual soft tissue control is established then this is where the soft tissue spline information (knots and coefficients for each segment of the spline) is maintained. If gain scheduling is enabled then this section of the database also maintains the gain schedule and control variable set-points. The information stored in this section of the database is maintained in user units. At down load time, the calibration database is referenced and appropriate conversions are made to inform the controller in machine units reflecting the current calibration of the system. This section of the database is designed to be user configurable and it is expected that a variety of operating scenarios for different testing purposes will be established. This data is maintained in a user named file structure that may be recalled to setup the controller (and hence the simulator) configuration in a repeatable manner.

The waveform ensemble for all of the controller channels is maintained in separate flat files which may be devised to represent different physiological functions such as walking, sitting, and stair climbing, as required by the tester. Each waveform is comprised of 256 points representing the time sequence of force, torque, displacement or angle required to drive the machine's actuators. This database is coordinated with the configuration database and the calibration database at download time to ensure properly calibrate operation.

A utilities database maintains programmable event detection and event response information used to detect component failure and to prevent specimen damage from unforeseen overload conditions. The utilities database also maintains information for programming the start and stop behavior and transitions between waveform files.

Programming of and operation of the virtual soft tissue controller (and hence the simulator machine) is accomplished through a number of user interface screens and control panels some of which are displayed in FIG. 5. FIG. 5A shows the realtime display with the Program Mode control panel displayed. The program Mode control panel allows the user to select a program which sequences up to 12 different waveforms representing different loading scenarios. By varying the loading scenarios more realistic lifetime wear characteristics are obtained. This technique has been adopted by several implant manufactures to more fully understand the wear characteristics of their implant devices. Additional operating control panels are available for setup, tuning and calibration of the machine. Each of these panels works interactively with the appropriate database to maintain a record of the information and settings for future application.

Figure 5A:
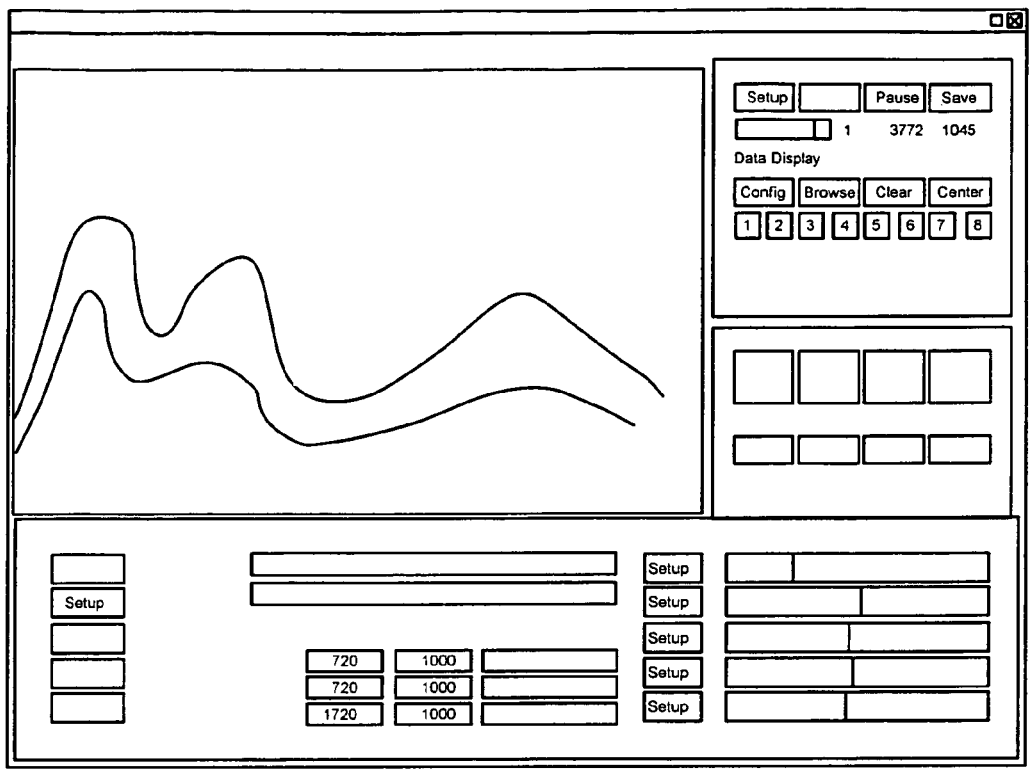
FIGS. 5A-5D illustrate user-interface screen shots for one embodiment of a virtual soft tissue simulator control system.
Figure 5B:
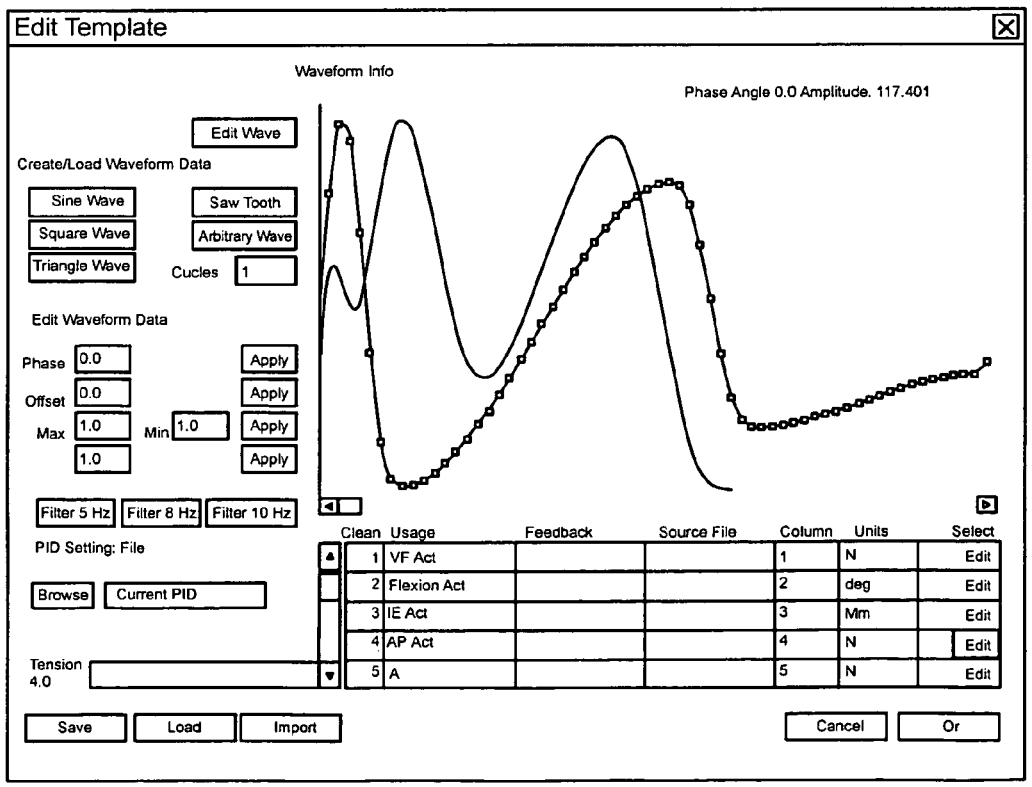

FIG. 5B illustrates the Template Editor screen which is used to create the driving waveform ensemble required to control the simulator through one cycle of motion. Waveform data may be imported from text file sources, created using several built in function generators or manually entered and manipulated using the editors drag and drop second order interpolation controls. Once created the waveform ensembles are saved to file and may be specified in program mode or individually to control the machine's actuators.

Figure 5C:
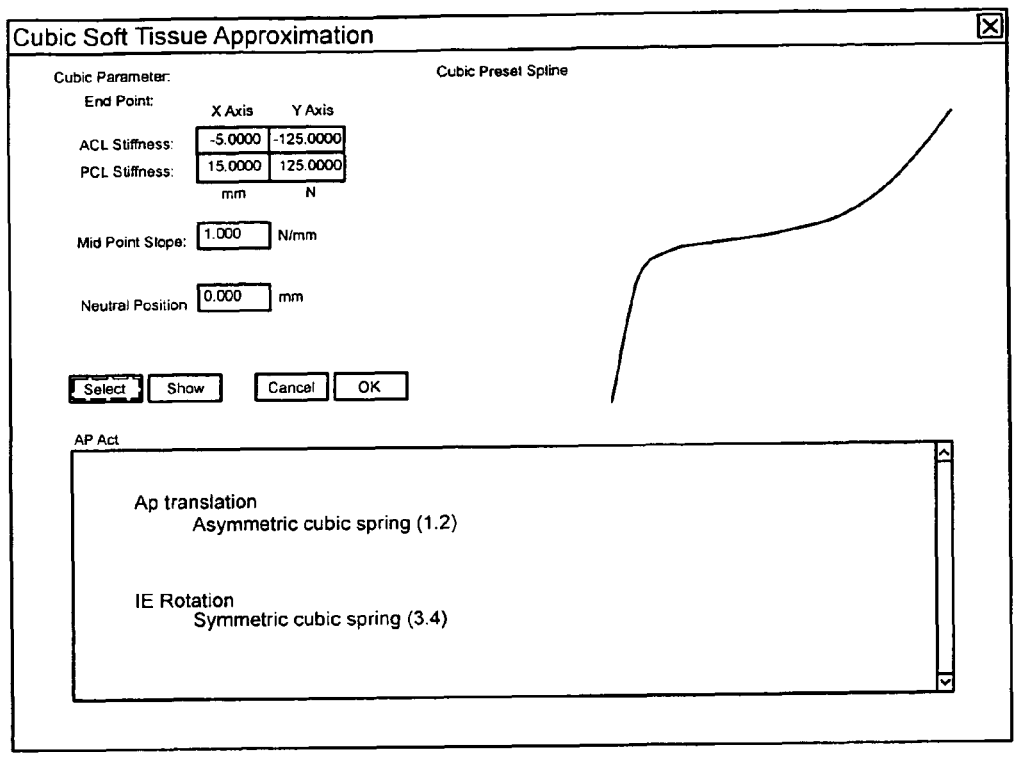
Figure 5D:
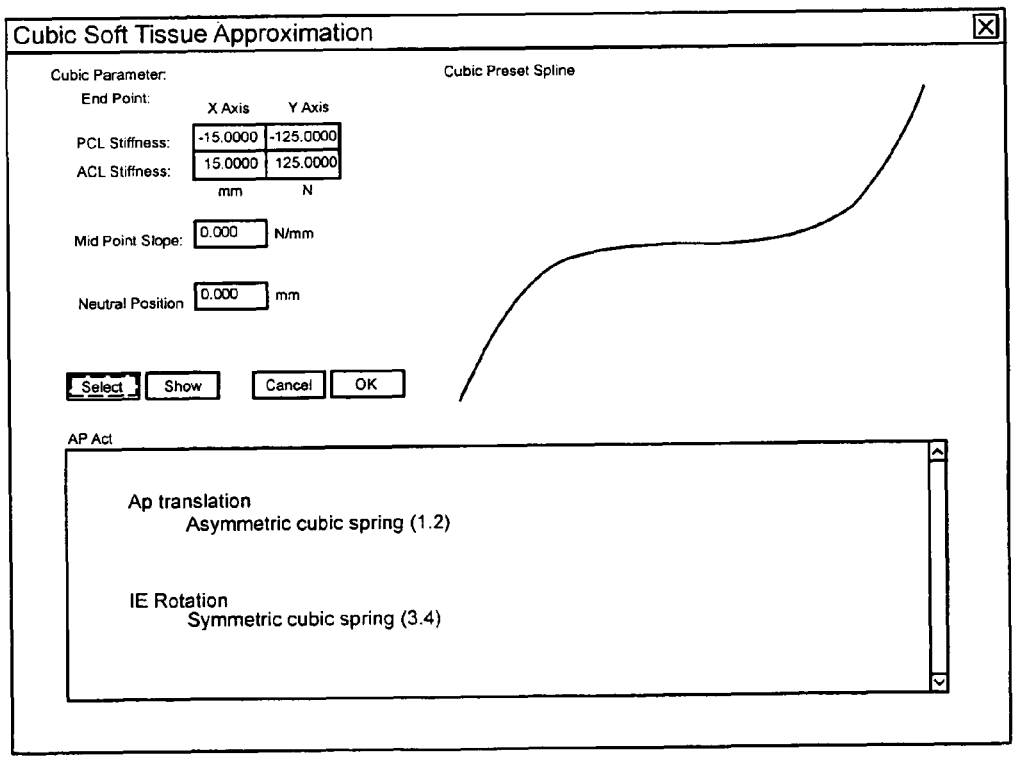

FIGS. 5C and 5D illustrate the Soft Tissue editor which allows the user to establish the soft tissue characteristics for a given actuator channel. Each actuator channel is independently controlled via the load displacement curves specified here. Several canned relationships for AP and IE load displacement have been devised based on the literature. These relationships may be selected, viewed and applied to the control of the selected actuator. For more advanced work the spline knots and coefficients may be entered as calculated elsewhere to satisfy the users requirements.

FIG. 5C shows an asymmetric cubic relationship which represents the soft tissue characteristics following PCL retaining arthroplasty. FIG. 5D shows a symmetric cubic relationship which represents the soft tissue characteristics following PCL sacrificing arthroplasty. These are only two of the many possible load displacement relationships that may be programmed using the soft tissue spline system. Canned splines can be built which represent linear models for AP and IE as specified by ISO 14243 and linear models with dead band as proposed by ASTM subcommittee F0.4 as well as the cubic relationships based on the literature.

Figure 6:
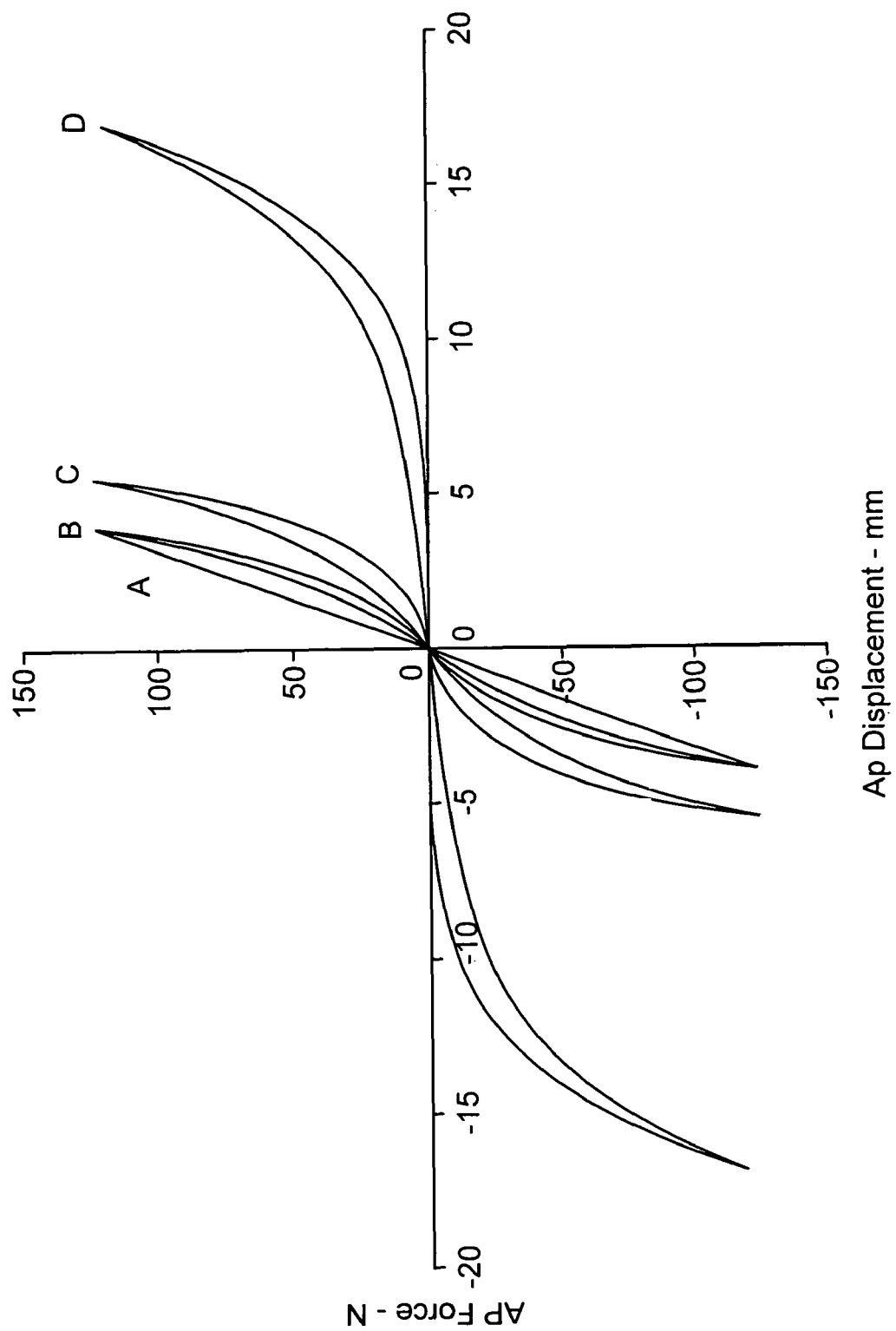
FIG. 6 illustrates force displacement curves for a human knee.

The force displacement and torque displacement characteristics of the knee have been extensively studied, and can be used to program the virtual soft tissue simulator of the present invention. One example of the force displacement characteristics of the soft tissue under various conditions is shown in FIG. 6. Curve A is the force displacement curve of a linear spring approximation; Curve B is the force displacement curve for intact ligaments with the tibia fixed in rotation; Curve C is the force displacement curve for intact ligaments with the tibia free to rotate; and Curve D is the force displacement curve for sectioned ACL and PCL. These curves can be used as a model for establishing the "virtual" soft tissue control characteristics for a given actuator channel.

Turning now to one example of a digital signal processor for use with the present invention, the DSP control and acquisition software can coded in native AD2181 DSP assembly language using fixed point arithmetic to provide the highest computational efficiency. A high level loop can provide a bus-based command interface that reads and responds to commands presented on the DSP's IDMA (direct memory access) port which is interconnected to an ELan SC310 processor for communication with a supervisory PC. At the low level, a single interrupt driven process can control all system control and data acquisition timing. The interrupt is generated at each completion of the data conversion process of the external ADC and thus is well synchronized with the acquisition process. A 2000 Hz, per channel, sample rate is used to acquire data from a total of 16 external analog inputs. Eight of these channels are reserved for high speed signals which can be selected to provide feedback for the controller PID loop channels. The high speed signals which can be selected to provide feedback for the controllers PID loop channels. The remaining eight channels are sub-multiplexed to provide a flexible data acquisition system to gather data from the simulators individual stations.

The output update rate is likewise 2000 samples per second per controlled channel. However there is a one sample time delay between acquisition of an entire dataset and outputting the updated control sample to the systems DAC channels. This results in a 500 microsecond phase error from the digital system which is negligible compared to the expected phase error of the servo-hydraulic system.

The DSP software can perform several different functions in real time (at the 2 kHz update rate) as listed below:
Read data input from the ADCs
Real time acquisition
Data scaling and offset correction
Event monitoring
Digital filtering
Waveform generation
Proportional, integral, derivative control calculation
Update of adaptive control feed forward signal
Soft tissue spline calculation
Data transfer to the SC310
Data output to the DACs While these real time control processes are being carried out the DSP's outer loop remains ready to receive messages and control data from the supervisory PC via the communications processor and the IDMA bus interface.

To provide flexibility for this development project the various functional components of the DSP control code can be developed as independent calculation and control blocks with mapable inputs and outputs. A simple look up table scheme provides redirection of the various control block input and outputs with minimal computational overhead. This scheme permits the exploration of various nested control scenarios for implementation of the virtual soft tissue scheme.

Figure 7A:
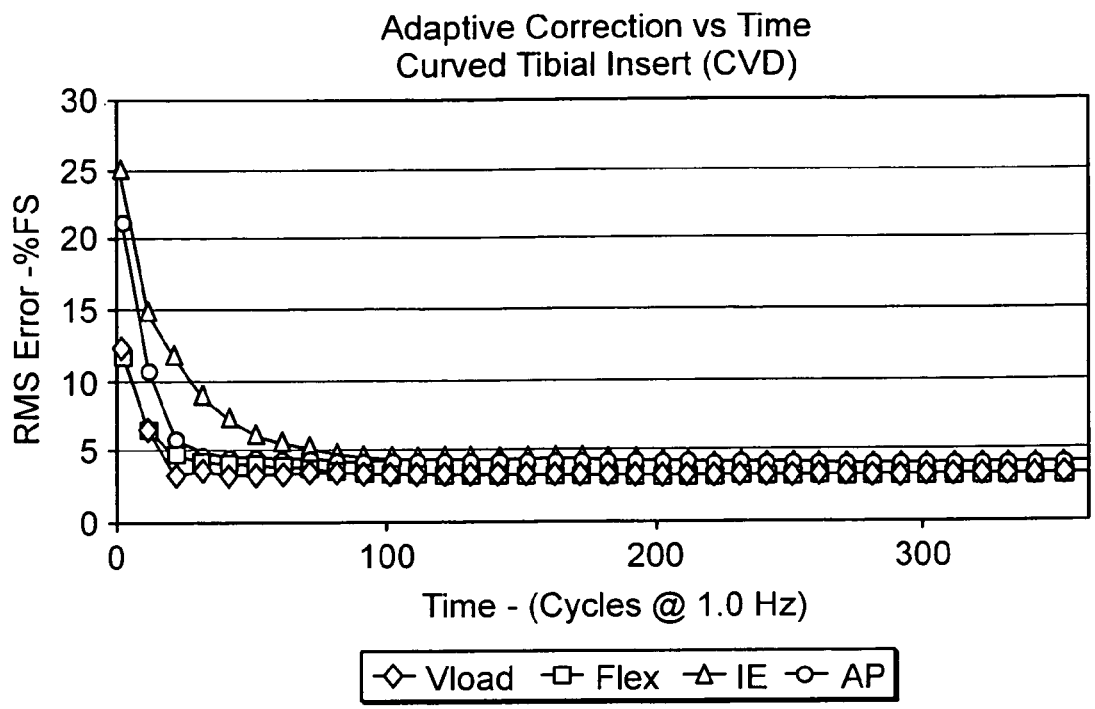
FIGS. 7A and 7B are graphs showing RMS error over time for a prosthetic device simulator machine having iterative learning control.
Figure 7B:
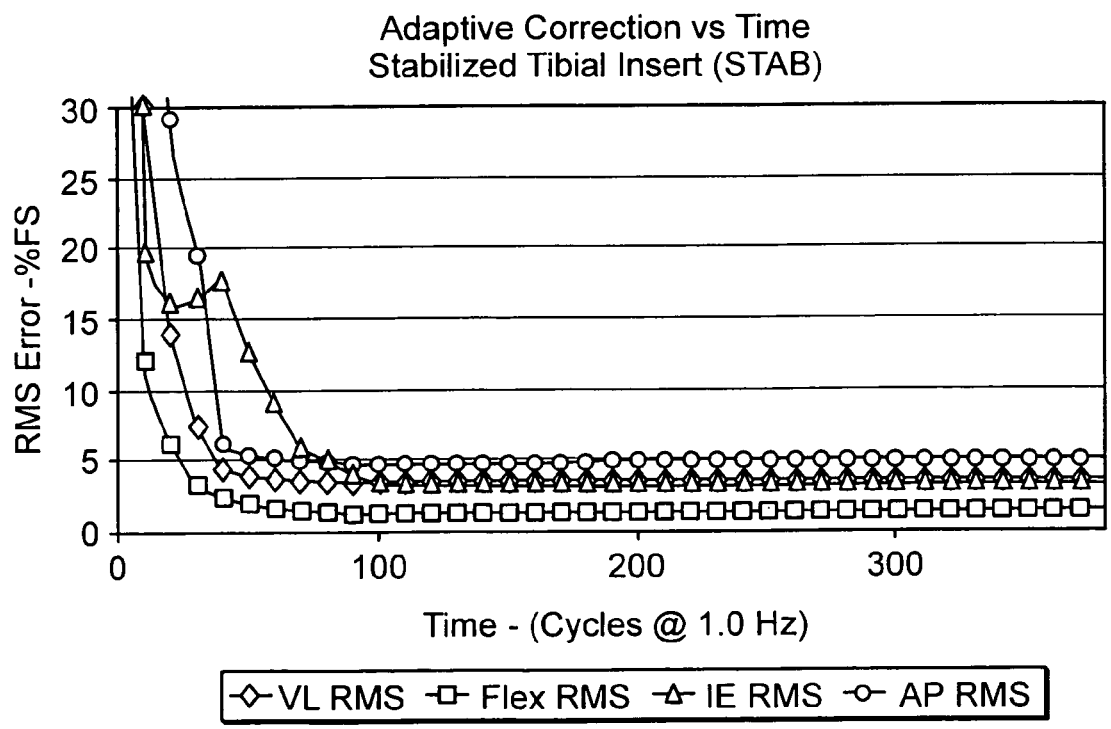

FIGS. 7A and 7B illustrate the "adaptive learning curve" of a simulator having iterative learning control, as discussed above. These figures show the measured RMS error of the control system as it evolves over time. The four actuator channels—axial force, flexion-extension, IE rotation, and AP translation—are displayed as individual series on the graph. All four channels show a rapid convergence to a steady-state RMS error of less than 5% within 30 cycles for the CVD device and 70 cycles for the STAB device. (The CVD device is a non-stabilized medium conformity device and the STAB device is posteriorly stabilized with moderate conformity).

This result is achieved with virtually no operator tuning. It is possible with increased adaptive control gains to achieve more rapid convergence, and at least initially, a lower RMS error. However, as adaptive control gain is increased the possibility of long-term instability grows. Several different adaptive control techniques were investigated. The objective was to minimize startup time, while maximizing long-term stability. Nonlinear gain control was implemented. This strategy involved using a quadratic function to control the gain based on the error amplitude. This provided a significant improvement in the initial speed of adaptation, but in general, made tuning more susceptible to instability. The best strategy for initial start up is to tune the traditional gain settings to provide reasonable tracking without the adaptive control algorithm. A slow startup time, allowing the waveform to develop to full amplitude over a 10 second period, permits a well-controlled development of motions. By maintaining relatively low adaptive control gains, long term stability is assured.

The adaptive control system renders the usability of the machine extremely high. In prior simulator systems with mechanical soft tissue constraint and conventional control, the typical setup time for a new prosthetic device is in the order of three days. Under iterative learning control, tuning and setup of the prosthetic device becomes virtually hands-off, frequently taking 60 seconds or less, while the tracking error is reduced to a level not previously obtainable by manual tuning. This represents a significant improvement in usability.

While this invention has been particularly shown and described with references to preferred embodiments thereof, it will be understood by those skilled in the art that various changes in form and details may be made therein without departing from the scope of the invention encompassed by the appended claims.

What is claimed is:

1. A simulator for an implantable prosthetic element, comprising
   a prosthetic drive mechanism that drives the implantable prosthetic element;
   a sensor that measures a force or torque applied to the implantable prosthetic element from the drive mechanism; and
   a control system responsive to the sensor and to a simulation input, the control system including a soft tissue model that accounts for soft tissue constraint and adjusts the drive provided by the drive mechanism in a repetitive programmed manner, the control system determining an error from a previous iteration of motion of the drive mechanism and including an accumulator that accumulates the error, the control system using the accumulated error to determine a drive signal applied in a subsequent iteration of motion of the drive mechanism.

2. The simulator of claim 1, wherein the soft tissue model comprises an algorithmic model of the soft tissue constraints imposed on the prosthetic element when implanted in a human or animal body.

3. The simulator of claim 1, further comprising a second sensor for measuring at least one of a position or orientation of the prosthetic element, the control system being responsive to the second sensor.

4. The simulator of claim 3, wherein the control system modifies the simulation input to account for soft tissue action based on a measurement of the second sensor.

5. The simulator of claim 3, wherein the control system comprises a nested loop design.

6. The simulator of claim 5, wherein an inner loop of the nested loop design comprises a proportional integral derivative (PID) controller that drives the drive mechanism based on the simulation input and feedback from the sensor for measuring the force or torque applied to the prosthetic element.

7. The simulator of claim 6, wherein an outer loop of the nested loop design comprises a virtual soft tissue controller that modifies the simulation input based on feedback from the second sensor and an algorithmic model of the soft tissue constraints.

8. The simulator of claim 3 wherein the second sensor is arranged to measure plural positions and plural orientations of the prosthetic element.

9. The simulator of claim 1, wherein the drive mechanism comprises a mechanical actuator.

10. The simulator of claim 1, wherein the simulation input comprises a waveform representing force or torque produced by active musculature forces of a human or animal representing physiological functions.

11. The simulator of claim 1, wherein the prosthetic element comprises a prosthetic knee.

12. The simulator of claim 1, wherein the prosthetic element comprises a prosthetic hip.

13. The simulator of claim 1, wherein the prosthetic element comprises at least one of a shoulder, elbow, spine, ankle, heart, and heart valve.

14. The simulator of claim 1 wherein the sensor is further configured to measure contact force and position, and the controller configured to calculate the soft tissue constraint from the measured position and adjust an active force with the calculated soft tissue constraint.

15. The simulator of claim 1 wherein the simulated input is software generated.

16. The simulator of claim 1 wherein the drive mechanism provides a repetitive force or torque to the prosthetic element.

17. A method for controlling a simulator for an implantable prosthetic element, comprising:
measuring force or torque applied to the implantable prosthetic element;
measuring at least one of position or orientation of the implantable prosthetic element;
driving implantable prosthetic element, in a repetitive programmed manner based on the measured torque or force, the measured position or orientation of the implantable prosthetic element, and an algorithmic model of soft tissue constraints, using an error in the measured force or torque, determined as a function of a difference between a simulation input and a sum of the measured force or torque and a force or torque determined based on the soft tissue constraints, to determine a drive signal for a subsequent iteration of the repetitive motion of the prosthetic element.

* * * * *